United States Patent

Ciaglia et al.

(10) Patent No.: US 6,637,435 B2
(45) Date of Patent: Oct. 28, 2003

(54) PERCUTANEOUS DILATIONAL DEVICE

(75) Inventors: Pasquale Ciaglia, deceased, late of Utica, NY (US), by Patricia F. Hague, legal representative; Melodee Deckard, Bloomington, IN (US); Mark J. Hiatt, Ellettsville, IN (US); Joseph P. Lane, Methuen, MA (US)

(73) Assignees: Cook Incorporated, Bloomington, IN (US); Sabin Corporation, Bloomington, IN (US)

( * ) Notice: Subject to any disclaimer, the term of this patent is extended or adjusted under 35 U.S.C. 154(b) by 0 days.

(21) Appl. No.: 09/729,506

(22) Filed: Dec. 4, 2000

(65) Prior Publication Data

US 2002/0066453 A1 Jun. 6, 2002

Related U.S. Application Data

(60) Provisional application No. 60/169,368, filed on Dec. 7, 1999.

(51) Int. Cl.[7] .............................................. A61M 16/00
(52) U.S. Cl. ............................. 128/207.29; 128/200.26
(58) Field of Search ....................... 128/200.26, 207.29, 128/207.14, 207.15; 606/108

(56) References Cited

U.S. PATENT DOCUMENTS

| | | | | | |
|---|---|---|---|---|---|
| 300,285 | A | * | 6/1884 | Russell | 128/207.29 |
| 460,987 | A | * | 10/1891 | Olivieri | 128/207.29 |
| 3,511,243 | A | * | 5/1970 | Toy | 128/207.29 |
| 3,754,554 | A | * | 8/1973 | Felbarg | 128/200.26 |
| 3,916,903 | A | * | 11/1975 | Pozzi | 128/207.29 |
| 3,957,055 | A | * | 5/1976 | Linder et al. | 128/200.26 |
| 4,211,234 | A | * | 7/1980 | Fisher | 128/200.26 |
| 4,364,391 | A | * | 12/1982 | Toye | 128/207.29 |
| 4,405,314 | A | * | 9/1983 | Cope | 606/108 |
| 4,449,522 | A | * | 5/1984 | Baum | 128/200.26 |
| 4,471,778 | A | * | 9/1984 | Toye | 128/207.29 |
| 4,978,334 | A | | 12/1990 | Toye et al. | 604/51 |
| 5,058,580 | A | | 10/1991 | Hazard | 128/207.15 |
| RE34,086 | E | * | 10/1992 | George | 128/200.26 |
| 5,186,168 | A | * | 2/1993 | Spofford et al. | 128/200.26 |
| 5,197,465 | A | * | 3/1993 | Montgomery | 128/207.29 |
| 5,217,005 | A | | 6/1993 | Weinstein | 128/200.26 |
| 5,217,007 | A | | 6/1993 | Ciaglia | 128/207.29 |
| 5,259,371 | A | * | 11/1993 | Tonrey | 128/200.26 |
| 5,279,285 | A | * | 1/1994 | Griggs | 128/200.26 |
| 5,623,924 | A | * | 4/1997 | Linderman et al. | 128/200.26 |
| 5,653,230 | A | | 8/1997 | Ciaglia et al. | 128/207.15 |
| 5,669,380 | A | | 9/1997 | Garry et al. | 128/207.14 |

FOREIGN PATENT DOCUMENTS

RU 1824188 A2 * 6/1993 ............ 128/207.29

OTHER PUBLICATIONS

Ciaglia Percutaneous Tracheostomy Introducer Set; Cook Critical Care Catalog.

* cited by examiner

*Primary Examiner*—Aaron J. Lewis
(74) *Attorney, Agent, or Firm*—Brinks Hofer Gilson & Lione

(57) ABSTRACT

A dilator (10) for creating tracheostomies in one pass. Dilator (10) includes a generally linear shaft (12) extending from a proximal end (14) and beginning at a distance therefrom, gradually and continuously through a curved distal portion (16) of continuously decreasing diameter (from about 38 french) to a distal tip portion (18) of small diameter of about 12 french at distal end (20). The outer surface of the insertable portion is treated or hydrophilically coated to minimize friction, and the gradual taper gradually widens the tracheal entrance opening (44) between tracheal rings (46,48) with minimal trauma. The wall thickness gradually decreases from the linear shaft (12) to the soft distal tip portion (18). The continuing curve of the distal portion (16) enables the increasingly longer inserted portion of the dilator to remain situated in the trachea (50) during insertion and for the distal tip portion to clear the posterior tracheal wall.

19 Claims, 3 Drawing Sheets

PERCUTANEOUS DILATIONAL DEVICE

RELATED APPLICATION INFORMATION

This application claims priority of Provisional Application Serial No. 60/169,368 filed Dec. 7, 1999.

TECHNICAL FIELD

This relates to the field of medical devices and more particularly to devices for percutaneous dilation.

BACKGROUND OF THE INVENTION

Certain medical devices are known that are used in the atraumatic dilation into a patient, such as percutaneously accessing a patient's air passageway and dilating an opening thereto, and forming an ostomy in the tracheal wall. A tracheal tube is then inserted through the ostomy and into the trachea to establish a passageway for unobstructed air flow. To minimize trauma to the patient, it has been found desirable to initially incise only a small opening as an entrance, and thereafter to enlarge the opening with further dilation.

Sold by Cook Critical Care, Division of Cook Inc., Ellettsville, Ind., is the "Ciaglia Percutaneous Tracheostomy Introducer Set", used for controlled percutaneous introduction of tracheostomy tubes. Sequentially sized dilators (from 12 french to 38 french) are advanced over a wire guide/guiding catheter system to facilitate gradual dilation of the tracheal entrance site to an appropriate size; one such dilator is shown in FIG. 1 and herein below described. The tracheostomy tube is placed by fitting the tube over the appropriate size dilator and advancing the tube into position. Each of the dilators includes an elongated linear shaft for manual gripping and manipulation, and is provided with a curved distal end concluding in a tapered tip that in use is coated with lubricating jelly, all to minimize trauma. First, the smallest dilator (12 french outer diameter) is first selected and placed over a guiding catheter and guide wire that extend through the opening until the tip is adjacent to the opening. Then the tapered tip is urged gently into the percutaneous incision and between adjacent ones of the trachea rings, and is gently withdrawn and reinserted to gradually widen the opening. The first dilator is then withdrawn and removed, and replaced by the next larger sized dilator and the procedure is repeated until the appropriate sized ostomy has been created.

It is desired to simplify the procedure used to create the ostomy and to shorten the length of time involved in its creation.

SUMMARY OF THE INVENTION

The present invention is directed toward a single dilator that is used to define the ostomy in one pass, thus replacing the several sequentially sized dilators and eliminating the repeated changing thereof, and thereby greatly simplifying the procedure and substantially shorten the time to define the ostomy, all serving to minimize patient trauma. The single dilator includes a soft, pliant tapered tip identical in shape and size and in tip inner diameter to those of the prior art dilators, and additionally includes a curved distal portion extending from the tapered tip toward the proximal end, and the generally linear shaft. The curved distal portion is tapered to extend from a diameter of 12 french (for example) adjacent the tapered tip, to a diameter of 38 french adjacent the linear shaft. Preferably both the curvature and the taper of the curved tapered distal portion from the distal tip to the shaft is gradual with no discontinuities. Also preferably, the curved tapered distal portion has a gradual transition in flexibility from very flexible at the short distal tip portion to generally rigid at the generally linear shaft portion, such as by gradually changing its wall thickness.

The resultant shape of the dilator of the present invention can be said to resemble the horn of a rhinoceros. Particularly useful for tracheostomies, the continuing curve of the distal end portion enables the increasingly longer inserted portion of the dilator to be situated in the trachea thus facilitating clearing the posterior tracheal wall.

Preferably the curved tapered distal portion and the short distal tip portion are provided with a hydrophilic coating that obviates the need for lubricating jelly and provides a very low coefficient of friction when hydrated, thus facilitating insertion into and withdrawal from the tracheal opening.

An embodiment of the invention will now be described by way of example with reference to the accompanying drawings.

DETAILED DESCRIPTION

Figure 1:
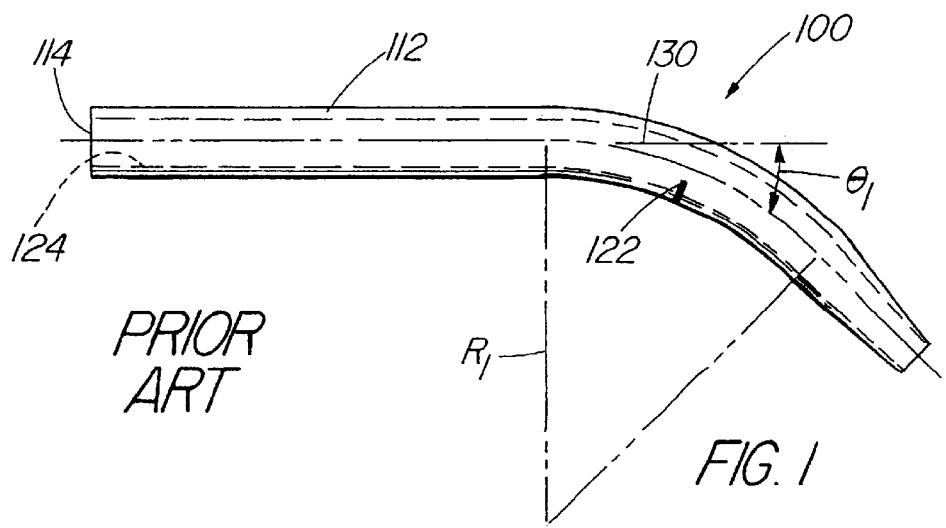
FIG. 1 is an elevation view of a Prior Art dilator.

Dilator 100 of FIG. 1 is a Prior Art dilator, namely, one of a series of dilators found in the "Ciaglia Percutaneous Tracheostomy Introducer Set" sold by Cook Critical Care, Division of Cook Inc., Ellettsville, Ind., used for controlled percutaneous introduction of tracheostomy tubes and having sequentially sized dilators (from 12 french to 38 french). Dilator 100 in particular is the largest of the series used last in the sequence to attain a tracheal entrance of about 38 french. Dilator 100 includes a shaft portion 112 extending from a proximal end 114, a tip portion 118 adjacent to distal end 120, and a curved intermediate section 130 extending between shaft portion 112 and tip portion 118. An insertion depth marking 122 is defined a distance of about 50 mm (2.0 in) from distal end 120, and on dilator 100 is positioned midway along curved intermediate section 130. A central passageway 124 extends from proximal end 114 to distal end 120.

Tip portion 118 on Prior Art dilator 100 is about 20.0 mm (0.79 in) in length and has a taper along each side of about 0.223 mm per mm (0.223 in per in), or about 12.6 degrees. (On smaller dilators of the "Introducer Set" the length of tip portion 118 is shorter while the taper remains the same; the insertion depth marking 122 may be along the linear shaft portion 112 on the smaller dilators.) Curvature of the centerline of curved intermediate section 130 is a radius R of about 80 mm (3.15 in) over an angular distance θ of about 20° to 40°. Wall thickness immediately at the distal end 120 is about 0.406 mm (0.016 in), and thickens over the portion extending for 5.99 mm (0.236 in.) from distal end 120 to a thickness of about 1.09 mm (0.043 in), which is the wall thickness of curved intermediate section 130 and the shaft portion 112, and at proximal end 114.

In Prior Art dilator 100, the outer diameter from the location from tip portion 118 is constant to proximal end 114 and is 38 french or 12.7 mm (0.491 in). Also, the wall thickness between tip portion 118 and proximal end 114 is constant at 1.09 mm (0.043 in). The durometer is measured at about 55 to 60 Shore D hardness.

Figure 2:
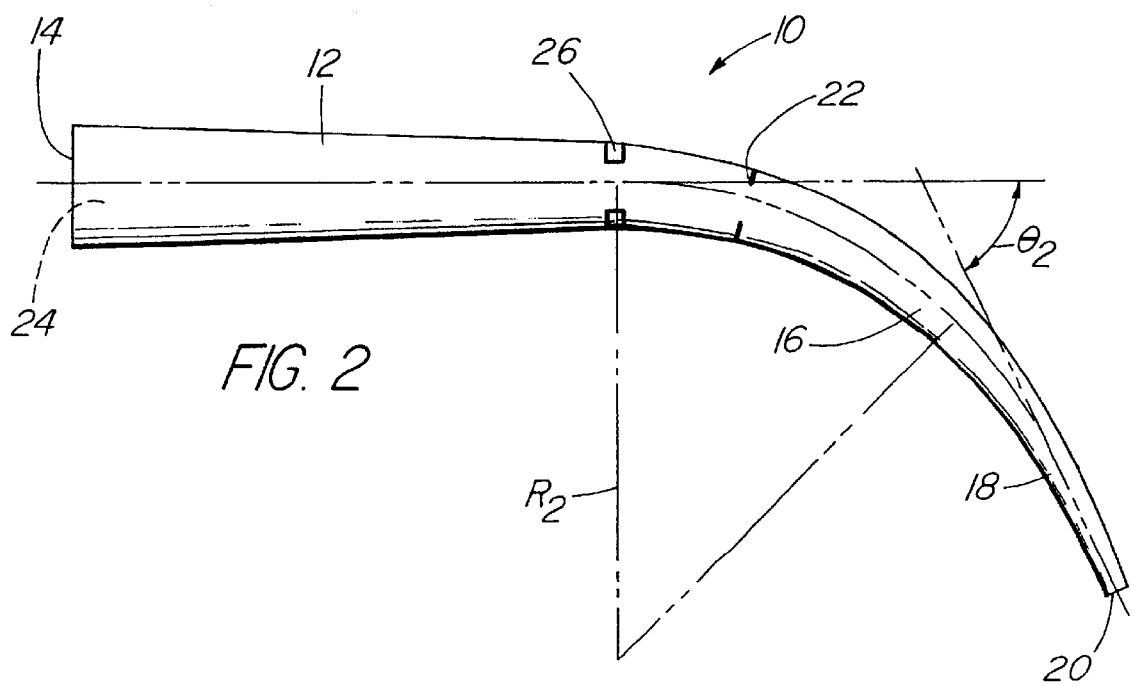
FIGS. 2 and 3 are elevational and longitudinal section views of the dilator of the present invention.
Figure 3:
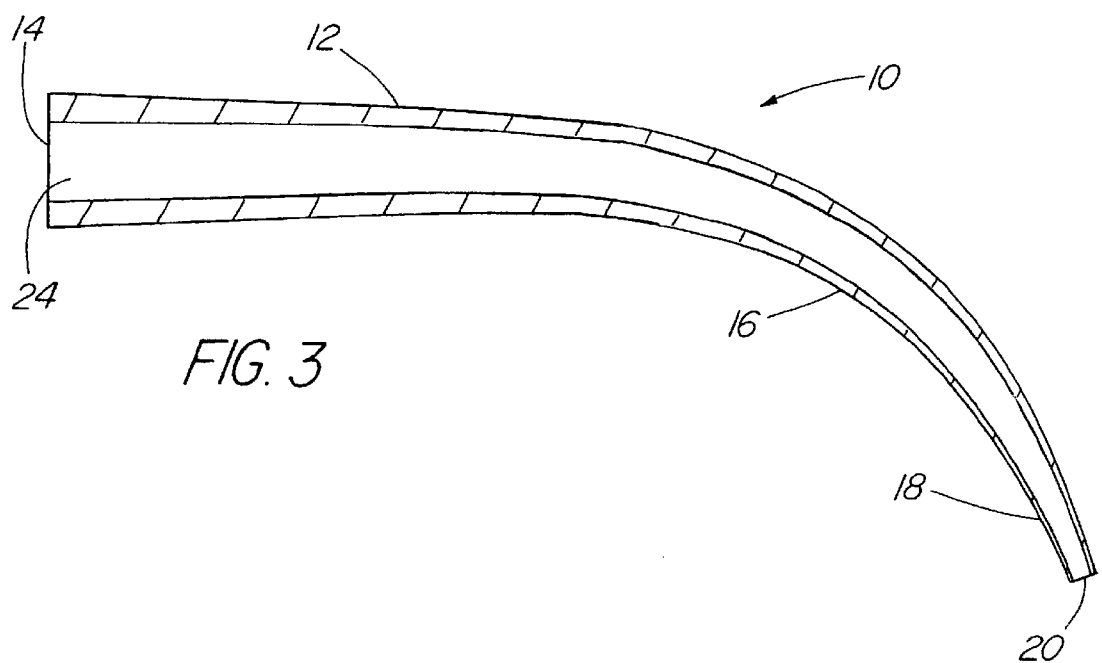
Figure 4:
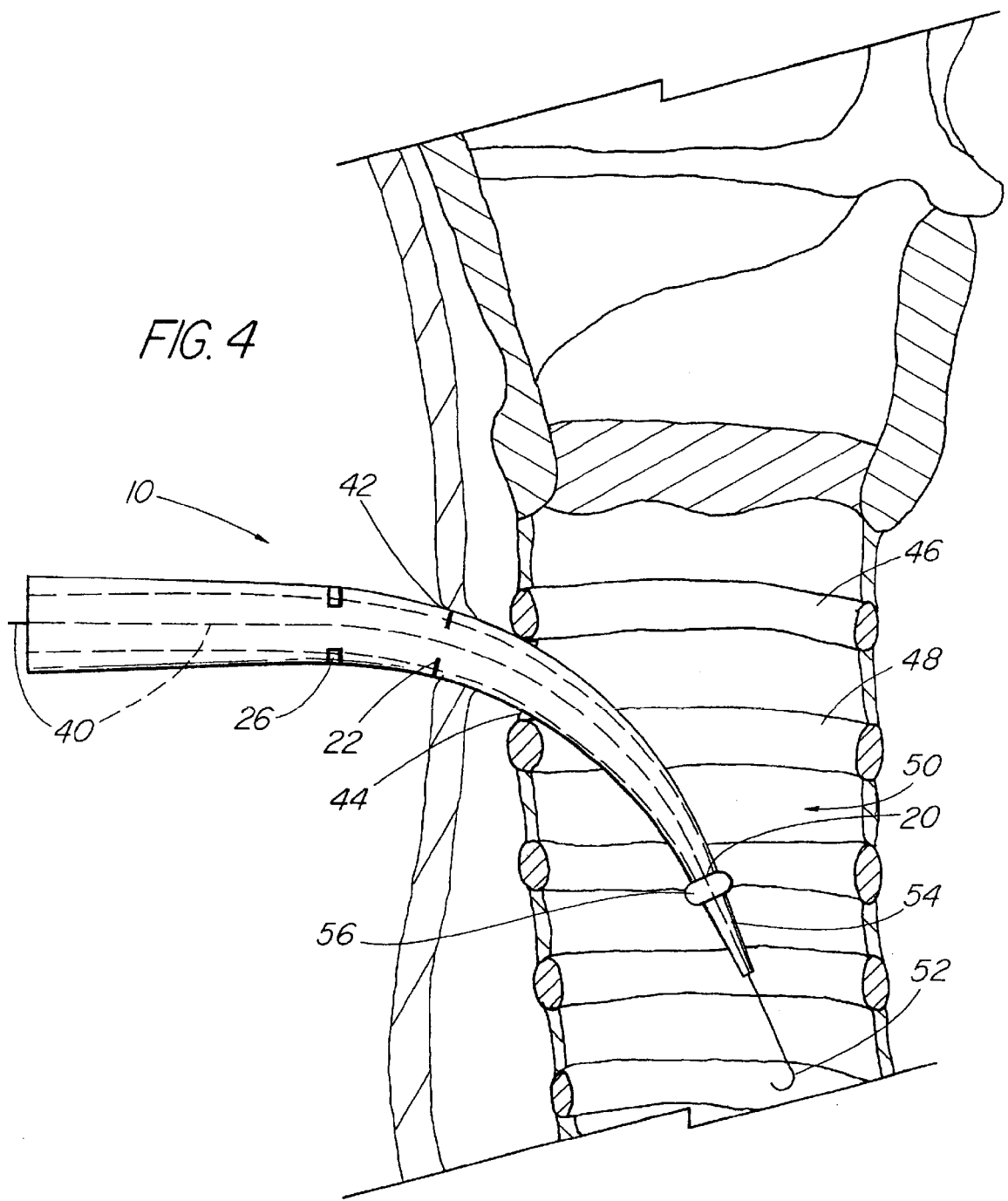
FIG. 4 is an elevation view of the dilator in position over a guide wire and extending through an entrance to a trachea.

Dilator 10 of the present invention is shown in FIGS. 2 to 4 and includes a shaft portion 12 extending from a proximal end 14, and a curved tapered distal portion 16 extending from shaft portion 12 to a small tip portion 18 at distal end 20. Demarcation 22 denotes the location at which the outer diameter is 38 french. A central passageway 24 extends completely there through from proximal end 14 to distal end 20. A marking 26 is identified toward proximal end 14 from demarcation 22 that indicates the recommended depth of maximum insertion into the skin, and that is at that location at which the shaft portion 12 and the curved tapered distal portion 16 meet.

Preferred dimensions of dilator 10 for use especially in tracheostomy procedures are: an overall length of about 196 to 210 mm (7.75 to 8.25 in); a length of about 110 mm (4.33 in) from distal end 18 to insertion depth marking 26; an inner diameter at distal end 20 of about 2.79 mm (0.110 in) and that extends the short length of flexible tip portion 18, about 3.18 mm (0.125 in); an outer diameter at distal end 18 of about 12 french or 4 mm (0.140 in); and an outer diameter at proximal end 14 of about 50 french or 16.5 mm (0.650 in), with an inner diameter of about 12.0 mm (0.473 in). The outer diameter at demarcation 22, as mentioned above, is about 38 french or 12.7 mm (0.491 in) and is located at about a distance of 80 mm (3.150 in) from distal end 20; and the inner diameter at demarcation 22 is about 7.72 mm (0.304 in).

The taper of the curved tapered distal portion 16 of the example described is about 0.056 mm per mm, or 3.19°. The taper may be within a range of tapers of between 1.7° and 10°. A very gradual taper such as about 1°00' may also, if desired, be used for the shaft portion 12 for facilitating removal of the molded dilator from the molding apparatus. Continuation of the taper in the proximal direction from curved tapered distal portion 16 also serves to permit, if necessary, further widening of the ostomy beyond 38 french, such as to 40.5 french at the insertion limit 26.

The curvature of curved tapered distal portion 16 may be a series of curves of different radii, or a complex curve, from distal end 20 at least to demarcation 22. The portion of dilator 10 between demarcation 22 and insertion limit 26 will extend, during use of the dilator, between the outer skin of the patient and the inside or anterior surface of the trachea of the patient. Also, the optimum curvature may be within a range such that the outer surfaces are within a zone of tolerance. While not susceptible of a precise mathematic definition, it is preferred that the curvature be complementary to the curvature of conventional curved tracheostomy tubes.

Preferably, the curved distal portion 16 transitions gradually from a very flexible short tip portion 18 at distal end 20, to a more rigid shaft 12 at insertion limit 26, thus having increasing rigidity in the direction extending away from distal end 20. Such flexibility transition may be generated such as providing a very small wall thickness at distal end 18 (e.g., 0.381 mm or 0.015 in) and greater wall thickness along shaft 12 of about 2.49 mm (0.098 in). Shaft 12 may also have a gradual taper, if desired. Dilator 10 may be made from polyurethane and be of softer durometer than prior art dilators, such as a durometer of about 43 Shore D hardness. Fabrication may be accomplished such as by molding the dilator initially in a linear tapered shape with appropriate wall thicknesses, and then inserting through the central passageway a rigid forming wire of stainless steel having an appropriate curved shape to elastically deform the dilator from its initial linear shape to generate the desired curve of the intermediate portion, and then post-curing the dilator at elevated temperatures with the forming wire in place, whereafter the dilator retains an appropriately curved shape. Sharp edges at the proximal end may be removed by abrasion, and the edges of the tip at distal end 20 may be rounded by careful application of localized heating and pressure to remove sharp edges.

Preferably, dilator 10 has a hydrophilic coating along curved tapered end portion 16 such as PHOTO-LINK coating material commercially available from SurModics, Inc., Eden Prairie, Minn. The material is a liquid mixture of PV05 Photo-Polyvinylpyrrolidone copolymer, PA05 Photo-Polyacrylamide copolymer, 2-propanol and distilled water. Upon the intermediate and distal end portions of the dilator being dipped into a bath of the mixture, with the distal end being occluded to isolate the interior surfaces, the coating on the dilator is cured by ultraviolet light at 150 wpi. Dilator 10 is preferably of radiopaque material, and it may be blue in color to minimize glare when viewed by an endotracheal bronchoscope that is in position in the patient above the tracheal ring 46 to view the procedure within the trachea from above the tracheal entrance.

FIG. 4 illustrates the use of dilator 10 positioned on and along a guide wire 40 that extends through incision 42 of a patient and in tracheal entrance 44 between adjacent tracheal rings 46,48, to introduce a tracheostomy tube (not shown) into trachea 50. Guide wire 40 includes a flexible J-shaped tip 52 and a guiding catheter 54 of 8.0 french over much of the guide wire. Guiding catheter 54 preferably includes an annular protrusion 56 there around to act as a stop for the distal end 20 of dilator 10. Dilator 10 is inserted over guide wire 40 until distal end 20 abuts annular protrusion 56.

With the curved tapered distal portion 16 hydrated such as by being dipped into sterile saline or water to hydrate and thus activate the hydrophilic coating thereon, dilator 10 is moved along guiding catheter 54 and the distal tip portion of dilator 10 is inserted into tracheal entrance opening. The assembly is then gently urged repeatedly into and partially withdrawn from the tracheal entrance opening 44 and prying apart tracheal rings 46,48 in an iterative procedure, increasing the insertion depth gradually each time until tracheal entrance opening 44 has been made sufficiently wide to enable a tracheostomy tube of appropriate size to be inserted there through. Once hydrated by being immersed into sterile saline or water, the outer surface of curved tapered distal portion is made very slippery without the use of lubricating jelly, with a substantially lowered coefficient of friction to minimize trauma to the patient. Marking 26 indicates the safety limit of insertion of the dilator into the patient's incision 42.

Dilator 10 is then removed from guide wire 40, and a loading dilator (not shown) of appropriate size is placed thereon, with the tracheostomy tube already placed on the loading dilator, extending through the widened tracheal entrance opening. Such a loading dilator may be similar to one of the larger Prior Art dilators as shown in FIG. 1. Thereafter, procedures are followed as with the prior art "Ciaglia Percutaneous Tracheostomy Introducer Set" instructions; the tracheostomy tube is translated along the loading dilator until fully inserted into the patient.

The dilator of the present invention results in a simplified procedure with fewer steps and shortens procedure time.

What is claimed is:

1. A dilator for tracheostomies, comprising:
   a member extending from a proximal end to a distal end and with a passageway extending therethrough defined by a wall having a thickness, the member having an elongate generally linear shaft portion extending from the proximal end and having a large diameter, a small diameter short distal tip portion adjacent the distal end, and a curved tapered distal portion extending from the generally linear shaft portion to the short distal tip portion, wherein the wall thickness of at least a portion of the curved tapered distal portion decreases from the generally linear shaft portion to the short distal tip portion.

2. The dilator of claim 1, wherein the curvature and the tapering of the curved tapered distal portion is gradual and continuous.

3. The dilator of claim 1, wherein at least the curved tapered distal portion has an outer surface that is lubricious.

4. The dilator of claim 3, wherein the outer surface is coated with hydrophilic material.

5. The dilator of claim 1, wherein the taper of the curved tapered distal portion is within a range of about 1.7° to about 10°.

6. The dilator of claim 5, wherein the taper is about 3.19°.

7. The dilator of claim 1, wherein the generally linear shaft portion has a taper of about 1°.

8. The dilator of claim 1, wherein the proximal end has an outer diameter of about 50 french.

9. The dilator of claim 1, wherein the distal end has an outer diameter of about 12 french.

10. The dilator of claim 1, wherein the short distal tip portion has a constant inner diameter and a tapered outer diameter.

11. The dilator of claim 10, wherein the short distal tip portion is very flexible and the generally linear shaft portion is generally rigid.

12. The dilator of claim 11, wherein the wall of the curved tapered distal portion has a gradual transition in its flexibility from very flexible at the short distal tip portion to generally rigid at the generally rigid linear shaft portion.

13. The dilator of claim 1, wherein a marking is provided on the outer surface of the member between the generally linear shaft portion and the curved tapered distal portion to indicate the safety limit of insertion into the incision.

14. The dilator of claim 1, wherein a demarcation is provided on the outer surface of the curved tapered distal portion to indicate the outer diameter at the demarcation.

15. A dilator for tracheostomies, comprising:
a member extending from a proximal end to a distal end with a passageway extending therethrough defined by a wall, the member having an elongate generally linear shaft portion extending from the proximal end and having a large diameter, a small diameter short distal tip portion adjacent the distal end, and a curved tapered distal portion extending from the generally linear shaft portion to the short distal tip portion;

the curvature and the tapering of the curved tapered distal portion is gradual and continuous;

the wall thickness of at least the curved tapered distal portion decreases from the generally linear shaft portion to the short distal tip portion;

the curved tapered distal portion has an outer surface that is lubricious;

the taper of the curved tapered distal portion is about 3.19°;

the short distal tip portion is very flexible and the generally linear shaft portion is generally rigid and the curved tapered distal portion has a gradual transition in its flexibility from very flexible at the short distal tip portion to generally rigid at the generally linear shaft portion; and a marking is provided on the outer surface of the member between the generally linear shaft portion and the curved tapered distal portion to indicate the safety limit of insertion into the incision.

16. A dilator for tracheostomies, comprising:
a member extending from a proximal end to a distal end and with a passageway extending therethrough defined by a wall having a thickness, the member having an elongate generally linear shaft portion extending from the proximal end and having a large diameter, a small diameter short distal tip portion adjacent the distal end, and a curved tapered distal portion extending from the generally linear shaft portion to the short distal tip portion, wherein the wall thickness of at least the curved tapered distal portion decreases from the generally linear shaft portion to the short distal tip portion, the short distal tip portion being very flexible and the elongate generally linear shaft portion being generally rigid and the curved tapered distal portion having a gradual transition in flexibility from very flexible at the short distal tip portion to generally rigid at the generally linear shaft portion.

17. The dilator of claim 16, wherein at least the curved tapered distal portion has an outer surface that is lubricious.

18. The dilator of claim 17, wherein the outer surface is coated with hydrophilic material.

19. The dilator of claim 16, wherein a marking is provided on the outer surface of the member between the generally linear shaft portion and the curved tapered distal portion to indicate the safety limit of insertion into an incision.

* * * * *